United States Patent [19]
Armini

[11] Patent Number: 5,919,126
[45] Date of Patent: Jul. 6, 1999

[54] CORONARY STENT WITH A RADIOACTIVE, RADIOPAQUE COATING

[75] Inventor: Anthony J. Armini, Manchester, Mass.

[73] Assignee: Implant Sciences Corporation, Wakefield, Mass.

[21] Appl. No.: 08/912,762

[22] Filed: Aug. 18, 1997

Related U.S. Application Data

[60] Provisional application No. 60/051,861, Jul. 7, 1997.

[51] Int. Cl.$^6$ .................................................. A61M 5/00
[52] U.S. Cl. ................................................................ 600/3
[58] Field of Search .......................... 600/1, 3; 606/108, 606/139, 191, 198, 194; 623/1, 12

[56] References Cited

U.S. PATENT DOCUMENTS

| | | | |
|---|---|---|---|
| 4,469,483 | 9/1984 | Becker et al. | 604/280 |
| 4,584,991 | 4/1986 | Tokita et al. | 128/1.1 |
| 4,586,490 | 5/1986 | Katz | 128/1.1 |
| 4,660,547 | 4/1987 | Kremer, Jr. | 128/1.1 |
| 4,714,074 | 12/1987 | Rey et al. | 128/1.1 |
| 4,715,359 | 12/1987 | Ryo | 128/1.1 |
| 4,733,665 | 3/1988 | Palmaz | 128/343 |
| 4,739,762 | 4/1988 | Palmaz | 128/343 |
| 4,776,337 | 10/1988 | Palmaz | 128/343 |
| 4,793,348 | 12/1988 | Palmaz | 128/325 |
| 4,803,977 | 2/1989 | Kremer, Jr. | 600/3 |
| 4,815,446 | 3/1989 | McIntosh | 600/3 |
| 4,881,937 | 11/1989 | van't Hooft et al. | 600/3 |
| 4,881,938 | 11/1989 | van't Hooft | 600/3 |
| 4,946,435 | 8/1990 | Suthanthiran et al. | 600/3 |
| 4,969,863 | 11/1990 | van't Hooft et al. | 600/3 |
| 5,030,194 | 7/1991 | van't Hooft | 600/3 |
| 5,034,005 | 7/1991 | Appling | 604/280 |
| 5,059,166 | 10/1991 | Fischell et al. | 600/3 |
| 5,176,617 | 1/1993 | Fischell et al. | 600/3 |
| 5,256,158 | 10/1993 | Tolkoff et al. | 604/280 |
| 5,360,443 | 11/1994 | Barone et al. | 623/1 |
| 5,382,261 | 1/1995 | Palmaz | 606/158 |
| 5,498,250 | 3/1996 | Prather | 604/280 |
| 5,522,880 | 6/1996 | Barone et al. | 623/1 |
| 5,606,981 | 3/1997 | Tartacower et al. | 128/772 |
| 5,607,442 | 3/1997 | Fischell et al. | 606/191 |
| 5,632,771 | 5/1997 | Boatman et al. | 623/1 |
| 5,656,036 | 8/1997 | Palmaz | 623/12 |

OTHER PUBLICATIONS

Tim A. Fischell, MD, et al., "Low–Dose, β–Particle Emission From 'Stent' Wire Results in Complete, Localized Inhibition of Smooth Muscle Cell Proliferation" in Circulation 90 pp. 2956–2963 (1994).

Joseph G. Wiedermann, MD, et al., "Intracoronary Irradiation Markedly Reduces Restenosis After Balloon Angioplasty in a Porcine Model" in JACC, vol. 23, No. 6, pp. 1491–1498, May 1994.

(List continued on next page.)

*Primary Examiner*—John P. Lacyk
*Attorney, Agent, or Firm*—Foley, Hoag & Eliot LLP

[57] ABSTRACT

A stent according to the systems and methods described herein may include a body formed from a non-radioactive structural material, a radiopaque material coating the body, and a beta-emitting radioisotope ion implanted into the radiopaque material. Optionally, an adhesion layer, such as titanium, vanadium, chromium, iron, cobalt, nickel, or some combination or alloy thereof, may be applied to the body to facilitate adhesion of the radiopaque material. The radiopaque material may include platinum, iridium, rhenium, gold, tantalum, or some combination or alloy thereof. The beta-emitting radioisotope may include sulfur-35 or phosphorous-32 and may be ion implanted into the radiopaque material.

17 Claims, 6 Drawing Sheets

OTHER PUBLICATIONS

Paul S. Teirstein, MD, et al., "Catheter–Based Radiotherapy to Inhibit Restenosis After Coronary Stenting" in *The New England Journal of Medicine,* vol. 336, No. 24 pp. 1697–1703 (1997).

John R. Laird, MD, et al., "Inhibition of Neointimal Proliferation With Low–Dose Irridation From a β–Particle–Emitting Stent" in Basic Science, pp. 529–536 (1995).

Vitali Verin, MD, et al., "Feasibility of Intracoronary β–Irradiation to Reduce Restenosis After Balloon Angioplasty" in Circulation, vol. 95, No. 5 pp. 1138–1143 (1997).

Hessel et al. "Antiography and Vasa Vasorum Blood Flow after Aortic Dilation," *Investigative Radiology* (Sep.–Oct) p. 404 (1978).

Goldberg et al, "In Vivo Aortic Smooth Muscle Cell (SMC) Kinetics: Responnse to Irradiation in the Rat," *Cell Tissue Kinet,* vol. 15, No. 6, p. 675 (1982).

Lee et al, "Effects of Laser Irradiation on Cardiac Valves Technique of Trans Catheter in Vivo Vaporization of Arotic Valve," *Laser Surg. Med.* vol. 3, No. 2, pp. 174–175 (1983).

Lee et al, "Laser Irradiation of Human Atherosclerotic Obstructive Disease: Simultaneous Visualization and Vaporization Achieved by a Dual Fiberoptic Catheter," *American Heart Journal,* vol. 105, No. 1, pp. 163–164 (1983).

Lee et al, "Effects of Laser Irradiation on Cardiac Valves Trans Catheter in Vivo Vaporization of Aortic Valve," *American Heart Journal,* vol. 107, p. 394 (Feb. 1984).

Solomon et al, "An In Vivo Method for the Evaluation of Catheter Thromboenicity," *Journal of Biomedical Materials Research,* vol. 21, pp. 43–57 (1987).

Rosch et al, "Glanturco Expandable Wire Strents in the Treatment of superior Vena Cava Syndrome Recurring after Maximum Tolerance Radiation," *Cancer* (Phila), vol. 60, No. 6, pp. 1243–1246 (1987).

Daniel et al, "A New Rapid Safe Method for Local Radiation of Intrathoracic Sites," *Am. Surg.,* vol. 55, No. 9, pp. 560–562 (1989).

COATED STENT WIRE

CORONARY STENT WITH A RADIOACTIVE, RADIOPAQUE COATING

CROSS-REFERENCE TO RELATED APPLICATION

This application is based on U.S. Provisional patent application Ser. No. 60/051,861, entitled, "Coronary Stent with a Radioactive, Radiopaque Coating", filed Jul. 7, 1997, pending.

TECHNICAL FIELD

This invention relates to the field of intra-arterial stents used to restore patency to coronary arteries and more specifically to radioactive stents with improved x-ray visibility.

BACKGROUND OF THE INVENTION

After balloon angioplasty, a metal tubular scaffold structure called a stent may be permanently implanted to physically hold open the repaired coronary artery. Unfortunately, up to 30% of such procedures result in reclosure (restenosis) of the artery within six months to one year. One solution to the problem is to provide acute local, postoperative radiation treatment of the site using a catheter tipped with iridium-192 radioisotope. In this method the iridium-192 tipped catheter is placed at the arterial site for thirty to forty minutes after stent deployment and then retracted. This type of acute high dose treatment using gamma radiation has been found to substantially reduce the rate of subsequent restenosis, as noted in Wiedermann, J. G. et al., "Intracoronary Irradiation Markedly Reduces Restenosis After Balloon Angioplasty in a Porcine Model," 23 J. Am. Coll. Cardiol., 1491–1498 (May 1994) and Tierstein, P. S. et al., "Catheter-Based Radiotherapy to Inhibit Restenosis After Coronary Stenting," 336 New England Journal of Medicine, 1697–1703 (Jun. 12, 1997).

An alternate method of addressing the restenosis problem is to form the structural material of the stent itself from a radioactive material as described by Fischell R. et al. in U.S. Pat. No. 5,059,166 (the '166 patent) and in U.S. Pat. No. 5,376,617 (the '617 patent). The '166 and '617 patents also describe a method of electroplating a radioactive material on the structural material of the stent. Each of these methods has certain drawbacks. Placement of radioactive material within the structural material of the stent can deteriorate the physical properties of the structural material, such as stiffness, and can present fabrication difficulties with respect to radiation exposure of workers during the manufacturing process. The electroplating process, on the other hand, may result in poor adhesion of the radioactive material, which could delaminate during insertion.

Moreover, an additional requirement for any clinically useful-stent is that it should have good x-ray visibility. A fairly thick (ten to fifteen micron) radiopaque coating of a high density, high atomic number metal such as gold, platinum, or iridium may be coated on the structural material of the stent in order to achieve visibility in an x-ray. Placing the radioactivity within the structural material, as taught by the '166 and '617 patents, may preclude coating the stent with a radiopaque metal. A high density metal that is approximately fifteen microns thick will absorb and reduce the kinetic energy of beta rays emitted from the structural material under the coating.

Further, the '166 and the '617 patents mention the possibility of plating the radioisotope $Au^{198}$ on the structural material of the stent. It is highly unlikely that plating of $Au^{198}$ would make the stent radiopaque because the coating would be less than a few angstroms thick. As noted by Fischell et al. in the article "Low-Dose β-Particle Emission From 'Stent' Wire results in Complete, Localized Inhibition of Smooth Muscle Cell Proliferation", 90 Circulation 2956–2963 (1994) (the Fischell article), radioactivity on the order of one microcurie is preferred for a coronary stent. Using an $Au^{198}$ plating solution containing typically 18 Ci/g of dissolved gold (following a two-week cooldown period after activation in a nuclear reactor), a total activity of 1 $\mu$Ci would require a total coating mass of 0.055 $\mu$g, which, when distributed over the surface of an entire coronary stent, would have a thickness of about one monolayer of gold. Such a thin layer would not add contrast in an x-ray picture of the stent. Moreover, $Au^{198}$ is not a pure beta ray emitter, it has numerous gamma rays, which may give a radioactive dose to the entire body of a patient instead of a localized dose to a target area in the coronary artery. $Au^{198}$ also has a half-life (2.7 days) that is too short to be practical for an intra-arterial coronary stent.

Another method mentioned in the Fischell article and further investigated by Laird, J. R. et al., in "Inhibition of Neointimal Proliferation with Low-Dose Irradiation from β-Particle Emitting Stent," 90 Circulation 529 (1996) (the Laird article), is to impregnate titanium stents with up to thirty atomic percent of stable phosphorous and subsequently activate the entire stent in a nuclear reactor to form the radioisotope $P^{31}$ within the titanium structural material. One of the disadvantages of the Laird method is that the massive quantity (30 at. %) of phosphorous required to make even 0.15 microcurie of $P^{31}$ may severely alter the structural strength of the stent itself.

The references discussed above do not suggest any way to adapt the radioactive stent embodiments of the '166 and '617 patents and also make the stent radiopaque. In the preferred embodiment of the '166 and '617 patents, the structural material is doped with an activatable element and then made radioactive in a nuclear reactor. The resulting radioactive stent would be extremely difficult to subsequently sputter coat with a thick (up to 15 micron) coating of gold. The radiation safety challenges for the factory workers would be considerable and would therefore render the technique impractical for mass production purposes. In addition, the sputter cleaning process, which would generally be necessary to achieve good adhesion, could emit radioactive structural material and contaminate the inside walls of the coating apparatus.

If the radiopaque metal is coated first and the coated stent is then placed in a nuclear reactor, the coating could activate gamma emitting isotopes to curie levels and render the stent undesirable for human use. For example, the thermal neutron reaction cross section for a gold radiopaque coating is 198 barns, which could activate a 15 $\mu$m thick gold coating to 10 tens of curies in a one week of irradiation.

Similar problems arise if the radioisotope is plated on the structural material of the stent, which is the alternate embodiment mentioned in the '166 and '617 patents. For this alternate embodiment, the sputter cleaning step prior to the radiopaque material coating could remove the radioactive material and distribute it throughout the inside walls of the coating apparatus. Gold is a very inert metal. As a result, if the gold is coated on the structural material first and then the radioactive material is plated on the gold outer surface, it could be extremely difficult to get the plating to adhere. The preferred radioactive plating of phosphorous-32 generally cannot be plated onto gold. The only radioisotope which can readily plate on gold is $Au^{198}$, but, as noted above, $Au^{198}$ is a gamma and beta ray emitter with a half-life (2.7 days) that is too short to be of clinical interest.

A method of plating a stent with a high density, radiopaque metal or alloy is disclosed in U.S. Pat. No. 5,607,442 to Fischell et al. (the '442 patent). The '442 patent describes a stent that is plated on its longitudinal wires with a radiopaque metal with a sufficient thickness so that the longitudinal wires will be clearly radiopaque in fluoroscopy. The circumferential wires of the stent are described as being plated with a much lesser thickness than the longitudinal wires so that they will not be distinctly radiopaque. The '442 patent describes the purpose of coating the longitudinal wires as being to assist the cardiologist in determining whether the stent has been fully and uniformly deployed throughout its entire length, thereby obviating the need for use of an intravascular ultrasound catheter. The '442 patent describes the purpose of coating the circumferential wires as being to avoid electrolytic corrosion of the stent by using a single metal outer coating on all stent surfaces, and, when plating with gold, to provide an attractive appearance for the stent. The '442 patent suggests that the circumferential wires should not be radiopaque because, if all the stent wires are radiopaque, such as if the stent is made from tantalum, then the stent may be so radiopaque as to obscure some of the lumen within the implanted stent.

The '442 patent also mentions in passing that the stent could include a radioisotope that is incorporated by ion implantation into the metal of the stent, or could include a radioisotope that is placed on the stent below an antithrombogenic coating. The '442 patent appears to indicate that the radioisotope should be ion implanted directly into the structural material of the stent. As noted above, ion implantation of radioactive material within the structural material of the stent can present fabrication difficulties. In addition, the high density radiopaque material plated on the longitudinal wires would absorb and reduce the kinetic energy of beta rays emitted from the structural material under the plating on the longitudinal wires, thereby causing a disparity in the spatial distribution of the beta radiation, which would be more intense longitudinally than circumferentially. Such spatial nonuniformity generally would be less desirable for reducing hyperplasia than a uniform distribution.

Another significant disadvantage of the methods disclosed in the references discussed above is the absence of any technique for assuring that the radiopaque coating sticks to the structural material of the stent. This disadvantage is particularly important when the radiopaque material is gold. In practice, gold plating, such as that disclosed in the '442 patent, cannot be electroplated directly onto stainless steel or nitinol. Moreover, the gold plating described in the '442 patent could be rubbed off during handling by medical personnel as well as during, and subsequent to, placement in a patient's body. Gold flaking could interfere with the deployment of the stent. If, for example, a proportionally substantial amount of the radiopaque gold on a longitudinal wire were to flake off, it could suggest, falsely, to the interventional cardiologist that the stent had not fully expanded. The cardiologist could then decide, reasonably but mistakenly, to inflate a very high pressure balloon within the stent, as disclosed in the '442 patent, in an attempt to correct the deployment of the stent. The stent also could be placed at the wrong position within the artery because the stent's length appeared shorter under fluoroscopy due to flaking off of the gold plating.

These difficulties may be overcome and a stent that is both radiopaque and radioactive may be fabricated using the present invention.

SUMMARY OF THE INVENTION

A stent according to the systems and methods described herein may include a body formed from a non-radioactive structural material, a radiopaque material coating the body, and a beta-emitting radioisotope ion implanted into the radiopaque material. The body of the stent may have a tubular mesh shape, a helical coil shape, or a variety of other shapes. Optionally, an adhesion layer may be coupled to the body and coupled to the radiopaque material. The adhesion layer may be formed of a material that includes titanium, vanadium, chromium, iron, cobalt, nickel, or some combination or alloy thereof. The adhesion layer may include a transition metal or alloy, and may be between approximately 100 to 3000 angstroms thick.

Optionally, the body of the stent may include a longitudinal portion and a circumferential portion, and the radiopaque material may be applied to coat both of the portions with substantially even thickness. The radiopaque material may include platinum, iridium, rhenium, gold, tantalum, or some combination or alloy thereof. The radiopaque material may be between approximately 1 micron and approximately 5 microns thick, or between approximately 1 micron and approximately 15 microns thick.

The beta-emitting radioisotope may emit substantially no alpha or gamma radiation, thereby facilitating use of the stent as an intra-arterial coronary stent. The beta-emitting radioisotope may include sulfur-35 or phosphorous-32. The beta-emitting radioisotope may be ion implanted to a depth of less than approximately 3000 angstroms into the radiopaque material, optionally with a source strength of between approximately 0.1 microcuries and 10 microcuries. The beta-emitting radioisotope may have a half life of less than approximately 100 days.

A method of fabricating a stent may include forming the stent from a non-radioactive structural material, coupling a radiopaque material to the structural material, and ion implanting a beta emitting radioisotope into the radiopaque material. The method may include coating the structural material with an adhesion layer and then coating the adhesion layer with the radiopaque material. Coupling the radiopaque material may include sputtering or electroplating the radiopaque material, or applying the radiopaque material as a coating with a thickness of less than approximately 15 microns. The method of fabricating may also include ion implanting the beta emitting radioisotope to a depth in the coating of less than approximately 3000 angstroms.

DETAILED DESCRIPTION OF THE PREFERRED EMBODIMENTS

Current stents are typically made from relatively light stiff metals such as titanium, nitinol, (50% Ti, 50% Ni) or stainless steel, which do not produce an adequate x-ray image in a fluoroscope device during the angioplasty procedure.

A gold coating of approximately ten to fifteen microns thick on the stent structural material may enhance the x-ray image significantly. Gold is a very soft metal, and a thickness of ten to fifteen microns should not contribute additional structural stiffness to the stent. The structural material of the stent should have considerable stiffness in order to hold open the elastic artery.

In order to effect good adhesion of the gold coating to the stent, it is desirable to first coat the structure with a thin coating of chromium or titanium about 3000 angstroms thick before depositing the thicker gold coating. Chromium has been found to promote adhesion of gold to stainless steel stents and titanium has been found to promote adhesion to nitinol stents. Both the adhesion promoting layer and the gold coating can be deposited using an unbalanced magnetron sputtering processing in vacuum.

The non-structural gold coating, however, may also be used as a host for the radioisotope. The radioisotope may be ion implanted, carrier-free, into the gold coating about 100 to 3000 angstroms below the gold outer surface.

The reverse configuration, i.e. ion implanting the radioisotope in the structural material of the stent then coating the structural material with ten to fifteen microns of gold, would not be preferred because the beta radiation kinetic energy and particle flux exiting the coating would be reduced due to the high atomic number (79) and high density of gold (19.3 g/cm$^3$). In addition, the process used to coat the radioactive stent with gold includes a sputter etch step, which would be used to clean and prepare the surface for the two subsequent coatings. This sputter etch cleaning step could remove the surface radioactivity and distribute it throughout the inside walls of the process chamber. One of the significant advantages of the unique configuration of the present invention is that the stent may be both radiopaque and radioactive with a beta emitting radioisotope.

A preferred process for fabricating the stent would be to form a cylindrical stent or tubular mesh stent from a non-radioactive structural material such as titanium, stainless steel, nitinol alloy or any other stiff alloy, sputter clean the alloy to remove the native oxides and about 100 angstroms of metal, and then coat the structural material with approximately 3000 angstroms of chromium or titanium to promote good adhesion, then coat the adhesion layer with approximately twelve microns of pure gold in a vacuum using an unbalanced magnetron sputter process (equipment available from AJA International, Scituate, Mass.).

Figure 1:
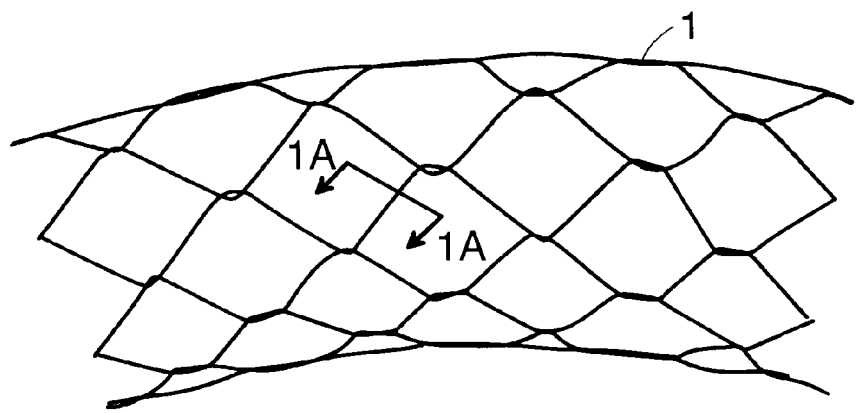
FIG. 1 illustrates a side-view and a cross-section of a single wire of a tubular mesh stent according to the present invention.
Figure 1A:
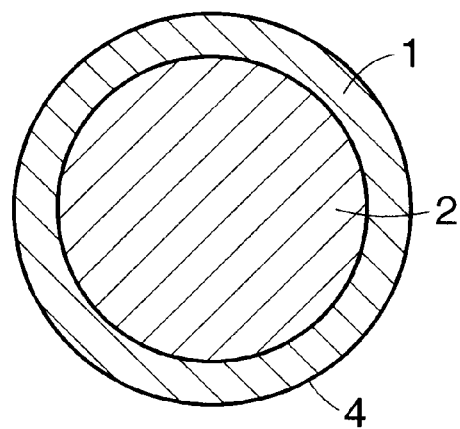
Figure 2:
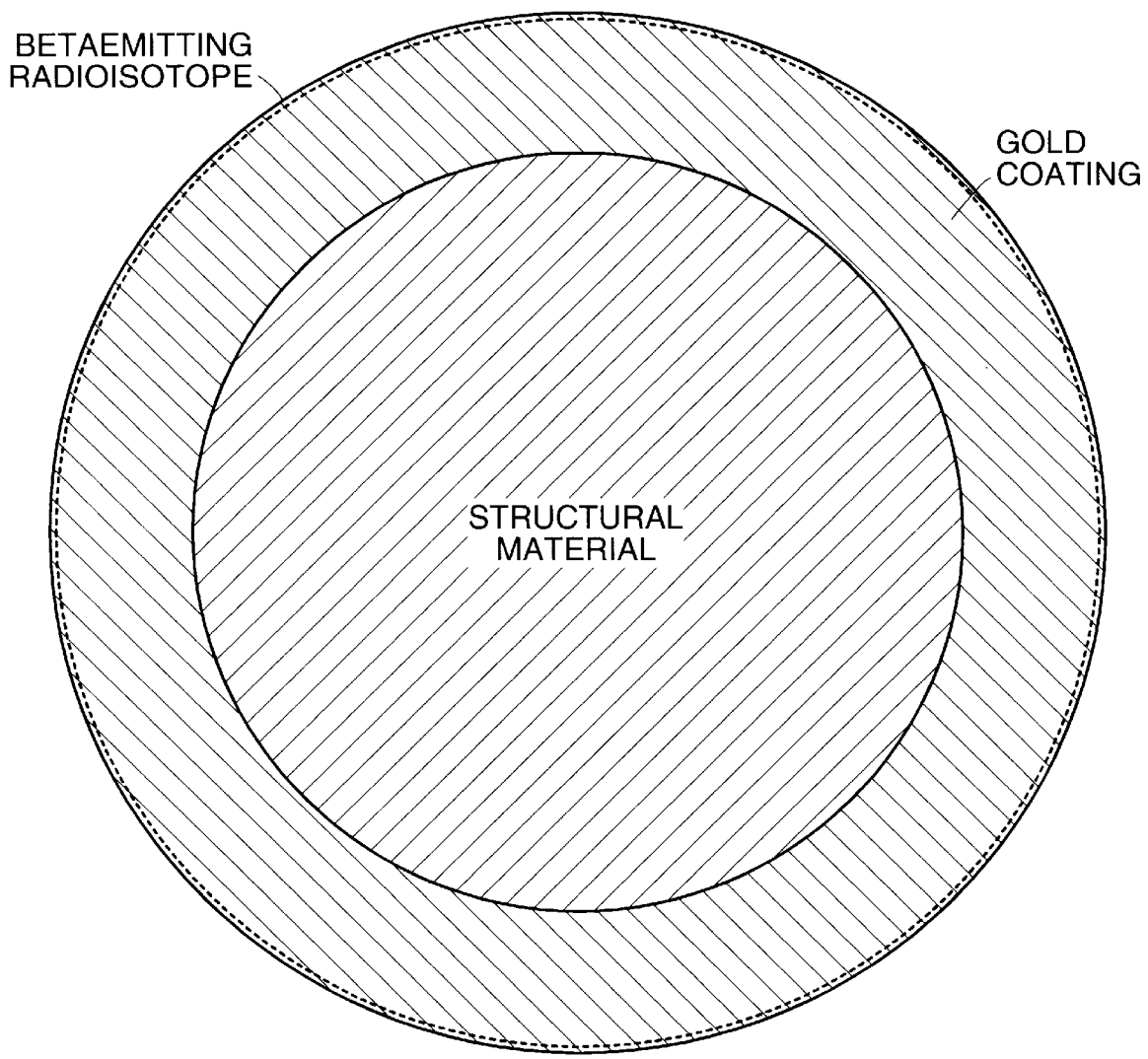
FIG. 2 illustrates an enlarged cross-section of a single wire of a stent according to the present invention.
Figure 3:
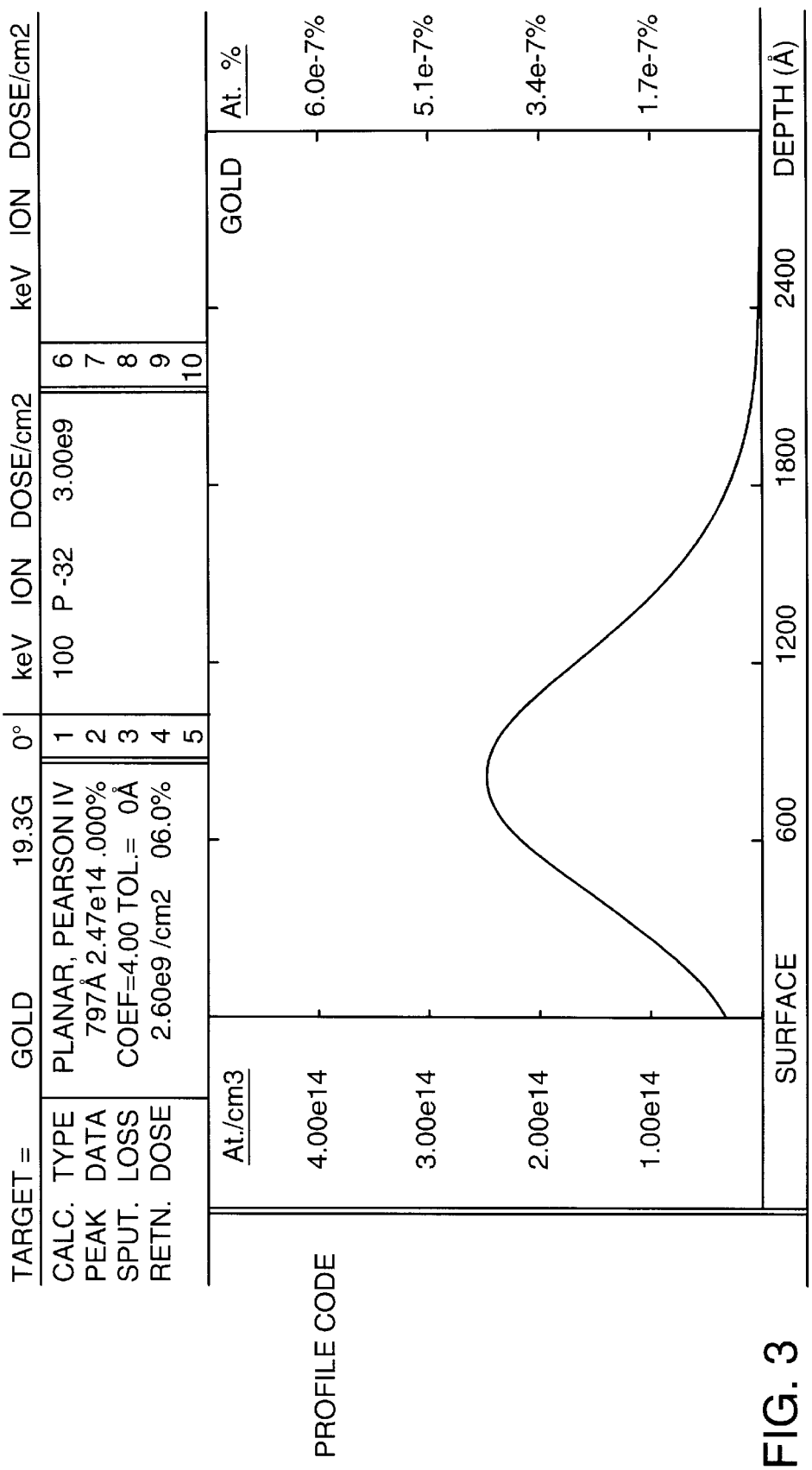
FIG. 3 shows an example of the depth distribution of a radioisotope $P^{31}$ when implanted in the gold coating.

The gold coating may then be ion implanted with the pure beta ray emitting radioisotope P$^{32}$ to a depth of 800 Å at the peak of its concentration. FIG. 2 shows the detail of a single wire in the stent. For a one microcurie stent, the peak P$^{32}$ concentration at 800 angstroms below the gold outer surface would be about 0.4 parts per million. FIG. 3 shows the depth distribution of P$^{32}$ atoms in the gold coating when implanted at 180 keV with a dose of 3×10$^9$ ions/cm$^2$, which produces one microcurie of radioactivity at the end of the implantation process.

The process for ion implantation of a radioisotope, such as phosphorous-32, can be done using a semiconductor ion implanter such as is readily available from Eaton Corp., Beverly, Mass. or Varian Corp., Gloucester, Mass. The radioactive starting material may be a gas that includes some phosphorous-32 radioisotope and is then fed into the gas inlet on the ion source. This process, however, generally is impractical for mass production because of the safety challenges involved in generating a radioactive ion beam in conventional semiconductor equipment using radioactive gases.

Ion sources in conventional ion implantation equipment need daily maintenance to replace consumed filaments and insulators. If the parts were also radioactive with phosphorous-32 containing gases, the operators could be exposed to toxic levels of radiation within several weeks of operation. It is therefore desirable, for practical manufacture of radioactive stents using this invention, to design and fabricate a special-purpose dedicated ion implanter to practice this invention. Such an ion implanter could have a specially designed ion source so that the operator could be shielded from radiation exposure during routine maintenance. In addition, the ion implanter could have a specially designed vacuum system to minimize the generation of radioactive pump oils.

Preferably, a custom made ion implanter could be used. The customized implanter could include a specially designed ion source with vacuum locks that permit the operator to change a filament or the radioactive charge without exposing the operator to excessive radiation or venting the vacuum chamber. An example of such a special ion source is described below.

The components of the ion source that routinely require maintenance may be affixed onto extensible probes that can be passed into the ion source vacuum system and positioned into their appropriate locations in the source. When service is required, the components may be removed. Typical ion source components include a cathode, a vaporizer, a sputter target, an electrostatic electron reflector, an anode, and a plasma chamber. These components need not all be present in a given implementation of an ion source.

A cathode is a source of electrons and is commonly formed from a hot filament composed of tungsten or tantalum metal, although a so-called hollow cathode may also be employed. A vaporizer is a heated oven in which the radioactive feedstock may be placed. There is typically a connection between the vaporizer and the plasma chamber of the ion source to permit passage of gas created by heating the feedstock. The vaporizer may also be located within the plasma chamber and use a variety of heating methods to heat the feedstock. Electrical resistance heating is typically employed when the vaporizer is external to the plasma chamber of the ion source while waste heat from operation of the source or heat from ion bombardment may be employed when the source of feedstock vapor is within the plasma chamber.

A sputter target is an alternate source of feedstock vapor. Excess ions fill the plasma chamber and are made to bombard the sputter target because of an applied or induced voltage. Sputtering liberates surface atoms from the sputter target, effectively creating a vapor of the feedstock. An electrostatic electron reflector is a surface that is isolated by electrical insulation so it is not directly connected electrically to the anode or cathode. However, plasma bombardment may indirectly induce a voltage relative to the anode or cathode.

The anode may be the plasma chamber itself or an independent electrode in the plasma chamber or ion source structure. The plasma chamber is a container in which the plasma created by the ion source is maintained prior to extraction and acceleration.

Figure 4:
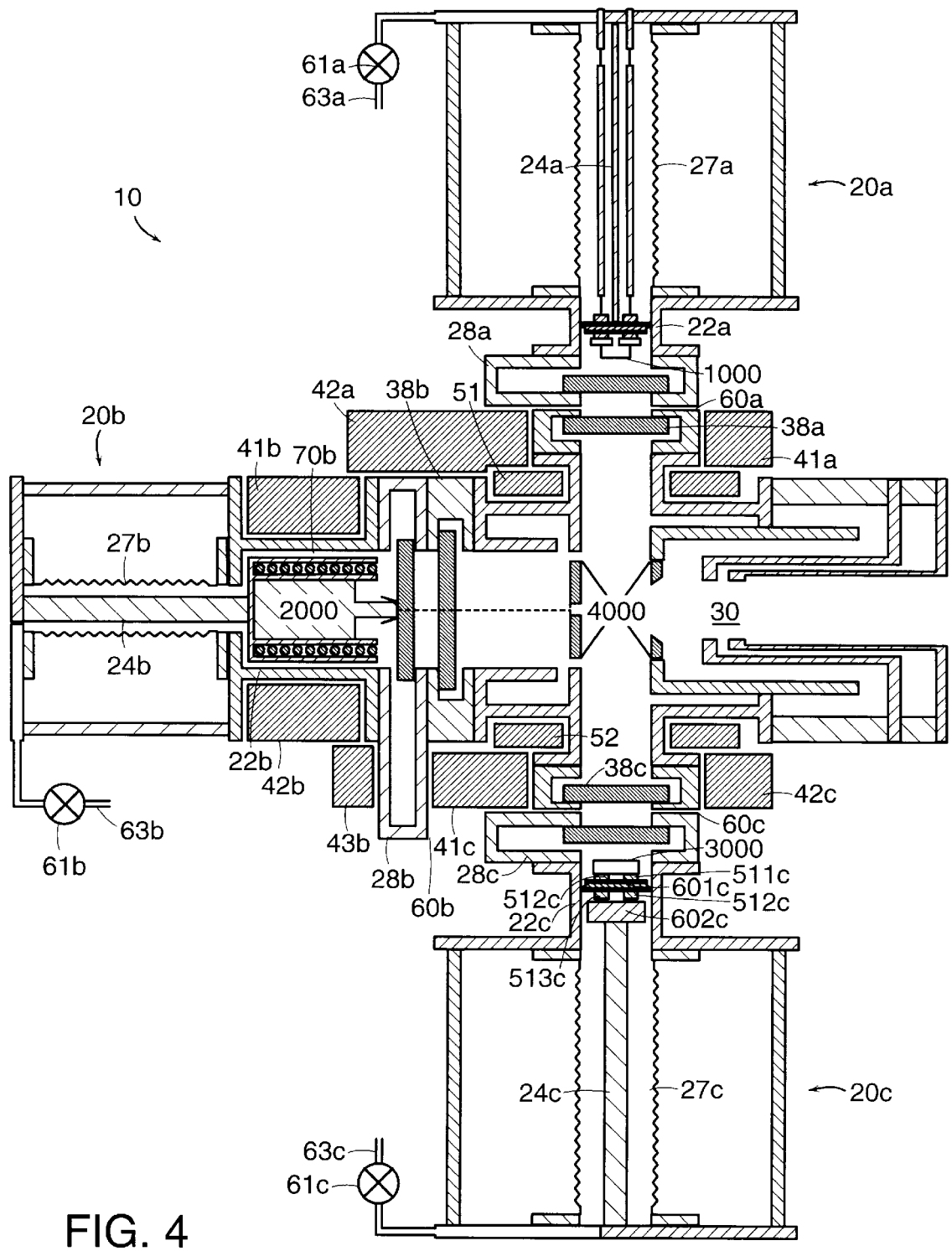
FIG. 4 is a schematic diagram of a cross-section of a custom made ion source for use in connection with the present invention. Three extensible probes are shown in a retracted position for servicing of the ion source.

FIG. 4 illustrates an embodiment of a customized ion implanter ion source 10. The source 10 includes a vacuum chamber 30, a hot tungsten filament cathode 1000 that may become eroded with use, an electrostatic electron reflector 3000 having insulators 511c, 512c, 513c, 514c that may also become coated with conducting material, a vaporizer 2000 for a radioactive elemental solid phosphorus 70b, and a plasma chamber 4000. The cathode 1000 is on an extensible probe 24c. The vaporizer 2000 is on an extensible probe 24b. The electron reflector 3000 is on an extensible probe 24c. Three sealable transfer containers 22a–c, each having sealable openings 28a–c, provide the capacity for containing radiation and radioactive particulates in addition to maintaining an inert gas atmosphere during transfer to a service area. Other radiation shielding 41a, 42a, 41b, 42b, 43b, 41c, 42c may be used to protect individuals while transferring the transfer containers 22a–c. Three valved openings 38a–c on the vacuum chamber 30 seal the vacuum chamber 30 from air after the extensible probes 24a–c are retracted. All of the extensible probes 24a–c in FIG. 4 are shown in the retracted position. Preferably, the valved openings 38a–c on the vacuum chamber 30 can be sealed adequately to maintain the vacuum in the system. The ion source 10 also contains three bellows 27a–c surrounding the extensible probes 24a–c. Joints 60a–c may be used to fasten the sealable openings 28a–c to the valved openings 38a–c. A magnetic field may be superimposed on the plasma chamber 4000, emanating from ferrous material poles 51, 52. Hand-operated valves 61a–c may be connected to vacuum and inert gas venting connections 63a–c, which could connect to a combined external pumping/venting assembly (not shown). Preferably, the removable enclosures 20a–c will have a minimum of extra hardware attached so they will be easier to lift.

The customized ion source 10 may be used in the following manner. First, the component 1000 may be mounted on the end of the extensible probe 24a. Then, the extensible probe 24a may be retracted into the vacuum compatible radiation shielded transfer container 22a and the transfer container seal in the sealable opening 28a may be closed. The transfer container 22a may be transferred to the ion source vacuum chamber 30 and attached onto the valved opening 38a. The vacuum and inert gas venting connection 63a may be attached to the valve 61a on the transfer container 22a to evacuate the transfer container 22a to a pressure similar to that of the ion source vacuum chamber 30. The transfer container sealable opening 28a and the valved opening 38a may then be opened. The extensible probe 24a is extended until it is in the correct position in the ion source 10. Other services that may be required by the component, such as cooling fluid or electrical lines, are then connected in a conventional manner. If appropriate, other components of the ion source may be connected and the ion source may be operated.

Maintenance of the component 1000 may be provided by first retracting the extensible probe 24a into the transfer container 22a and closing the valved opening 38a. Services may then be disconnected and the transfer container 22a may be vented with inert gas. The sealable opening 28a on the transfer container 22a may then be closed. The vacuum and inert gas line 63a may be disconnected from the valve 61a. The transfer container 22a may be disengaged from the valved opening 38a and the transfer container 22a may be transferred to a service area where an inert atmosphere is provided and/or where suitable radiation shielding and remote manipulation hardware is available. Also, the transfer container 22a may be opened to either air or to dry nitrogen, depending on whether the component 1000 is moisture sensitive.

The other extensible probes 24b–c, transfer containers 22b–c, and components 2000, 3000 may be operated in a manner similar to that described above for the extensible probe 24a, transfer container 22a, and component 1000. The ion source vacuum chamber 30 may be connected to a vacuum chamber assembly for a mass filter (not shown).

Figure 5:
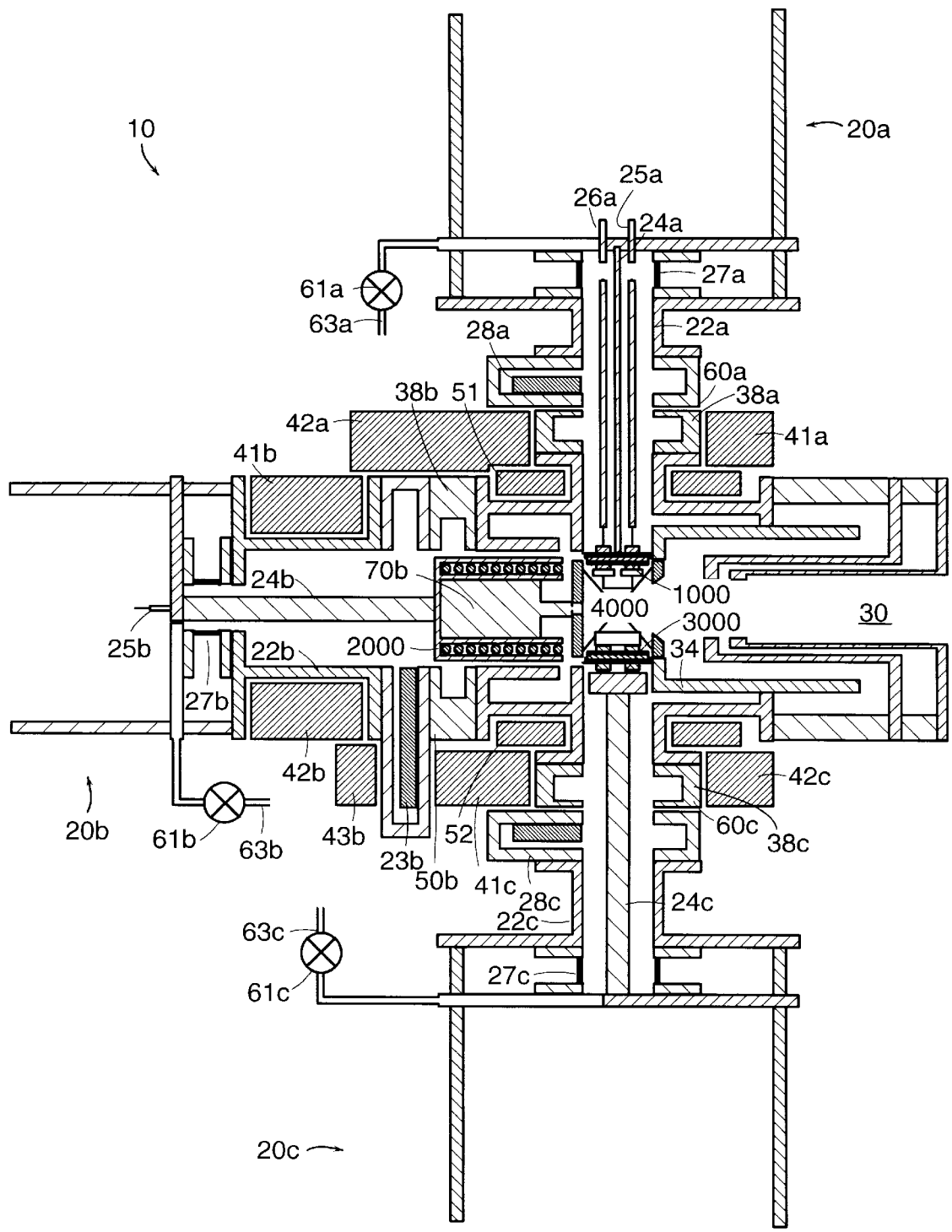
FIG. 5 is a schematic diagram of the ion source of FIG. 4 showing the extensible probes in an extended position for operation of the ion source.

FIG. 5 shows the ion source 10 of FIG. 4 in an operational position with the extensible probes 24a–c extended to connect with the plasma chamber 4000. In addition, the sealable openings 28a–c and the valved openings 38a–c are shown in an open position to facilitate extending the extensible probes 24a–c. The bellows 27a–c have been compressed and three connections 25a, 26a, 25b for services are shown. A baffle 34 also is shown in the ion source vacuum chamber 30. The shape of the baffle 34 and its location and placement within the ion source vacuum chamber 30 downstream of an orifice on the plasma chamber 4000 may help minimize leakage of radioactive phosphorus gas into areas of the ion source vacuum chamber 30 other than the zones where the ion beam must be transported. The ion source 10 may be operated in a conventional manner with a vacuum varying from approximately $10^{-5}$ torr where the ion beam hits the work piece (not shown) to approximately $10^{-2}$ torr in the plasma chamber 4000.

Figure 6:
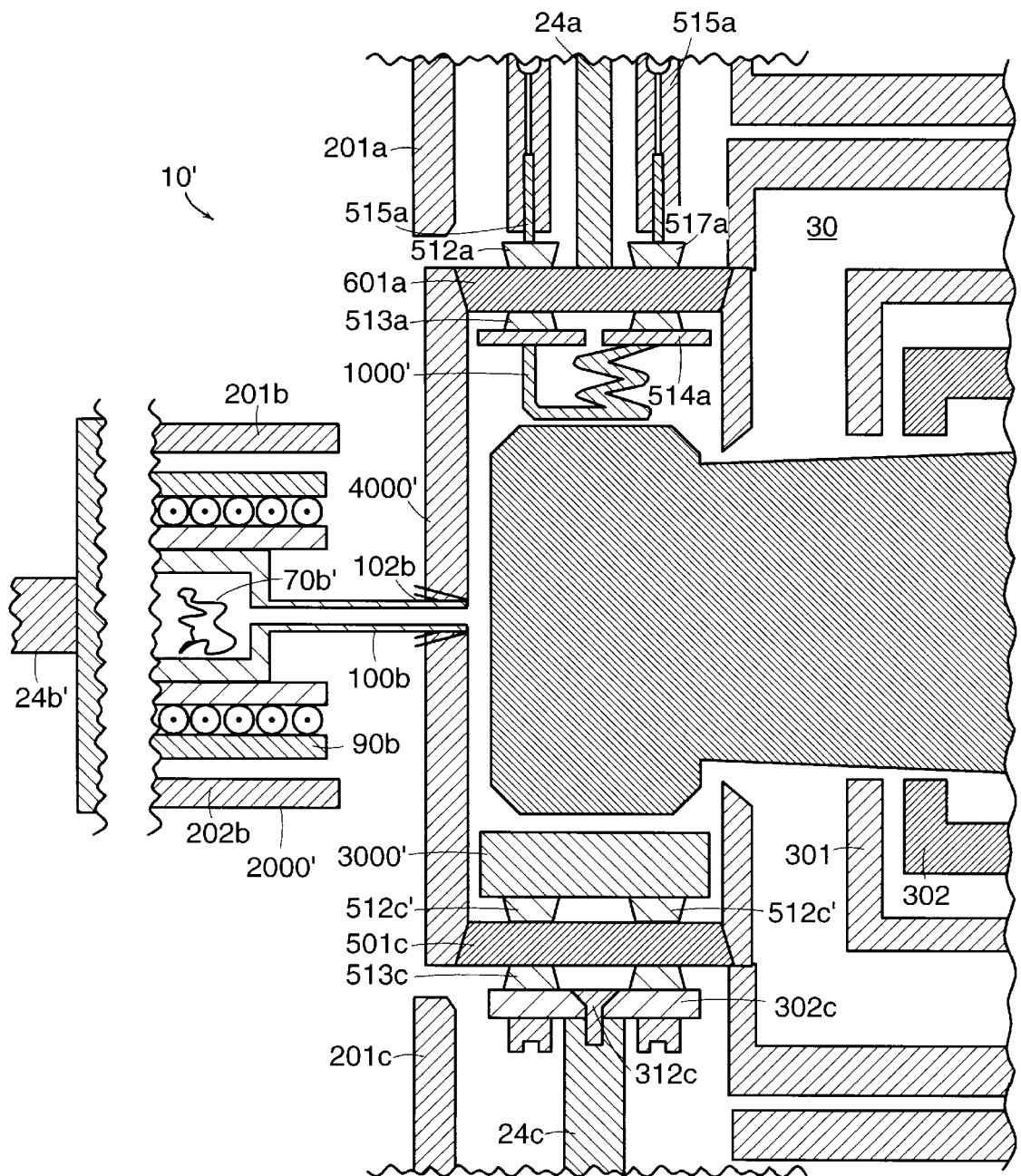
FIG. 6 is a schematic diagram illustrating an alternate embodiment for a plasma chamber of a custom made ion source.

FIG. 6 shows an interior portion of an ion source 10' that uses a hot filament cathode 1000' with a plasma chamber 4000' acting as an anode. A vaporizer oven 2000' may contain a solid phosphorus-containing compound 70b' which may be elemental phosphorus. A heater 90b may be used to raise the temperature of the phosphorus material 70b' until a sufficient vapor pressure and gas flow of phosphorus is obtained to operate the ion source plasma chamber 4000'. Phosphorus vapor may be passed into the plasma chamber 4000' through a tube 100b. The vaporizer 2000' may be attached to an extensible probe 24b' and extended towards the plasma chamber 4000'. Alignment may be facilitated by a pair of guides 201b, 202b. The vaporizer 2000' may preferably be unioned, or temporarily joined, to the plasma chamber 4000' using tapered joint 102b, which may make a substantially gas-tight seal and may be self-aligning.

A cathode 1000' may be placed on the extensible probe 24a' and an electrostatic reflector 3000' may be placed on the extensible probe 24c'. The cathode 1000' and the electrostatic reflector 3000' may be mounted on taper joint platforms 601a, 601c' and may be electrically insulated with ceramic insulators 511a, 512a, 513a, 514a, 511c', 512c', 513c', 514c'. A pair of guides 201a, 201c also may be included to assist in the positioning of the extensible probes 24a', 24c'. The guides 201a, 201c preferably may have beveled edges where needed to avoid accidentally entrapping the extensible probes.

It is desirable to avoid leaking radioactive phosphorus gas into areas of the ion source vacuum chamber 30 other than the zones where an ion beam 900 is transported in order to minimize possible contamination to workers during maintenance of the extensible components. Therefore, the vacuum chamber 30 may preferably be separated into two largely isolated volumes, one volume being the zone where the ion beam 900 is located and the second volume being the zone where the extensible probes 24a'–c' enter the vacuum chamber 30. FIG. 6 shows an example in which an extraction electrode 301 and a ground electrode 302 are connected to the plasma chamber 4000' downstream of the plasma chamber 4000'.

The detailed method of preparing the preferred embodiment of the radiopaque, radioactive stent of this invention would be as follows. First, an ordinary non-radioactive, non-radiopaque coronary stent made of stainless steel with dimensions of approximately 2 mm in diameter, 1.5 cm in length may be placed in a vacuum chamber of an unbalanced magnetron sputter coating apparatus. The apparatus may have two sputter sources, one for chromium and one for gold. The chamber may also contain a low energy "Kaufman" type ion source for sputter cleaning parts using an argon ion beam. While the stent rotates about its long axis, an ion source with an argon ion beam current density of approximately ten microamps per $cm^2$ at two keV may be directed at the rotating stent for approximately eight to ten minutes to remove the native oxide and to remove approximately 100 to 500 angstroms of stainless steel from the stent's surface for the purpose of making the surface atomically clean. The stent may then be coated with 3000 angstroms of chromium using the first sputter gun for approximately 10 minutes. The stent may then be coated with approximately 12 microns of pure gold using the second sputter gun in a one hour deposition period. During these coating runs, the stent may be biased with 100 volts of D.C., which generally produces better adhesion of each coating.

After these coatings, the stent may be removed from the coating apparatus and placed in the end station vacuum chamber of a special-purpose radioactive ion implanter similar to the implanter described above. While rotating, the stent may be exposed to a fluence of $6 \times 10^9$ $P^{32}/cm^2$ times pi (3.14159) (to account for the circumference of the stent) at a kinetic energy of 180 keV. The implantation process, done at an ion beam current density of approximately one picoampere per $cm^2$, may take approximately 50 minutes to complete. At the conclusion of the implantation process, the stent may have an activity of approximately two microcuries. The stent may then be shipped to a hospital and, after approximately two weeks (one half-life) on the shelf, it may have an activity of one microcurie and be ready for an angioplasty procedure.

While the invention has been disclosed in connection with the preferred embodiments shown and described in detail, various modifications and improvements thereon will become readily apparent to those skilled in the art. Accordingly, the spirit and scope of the present invention is to be limited only by the following claims.

I claim:

1. A stent comprising:

a body comprising a non-radioactive structural material;

a radiopaque material disposed on said body;

an adhesion layer coupled to said body and said radiopaque material; and a beta-emitting radioisotope ion implanted into said radiopaque material.

2. The stent according to claim 1, wherein said adhesion layer comprises at least one material selected from the group consisting of titanium, vanadium, chromium, iron, cobalt and nickel.

3. The stent according to claim 1, wherein said body comprises a longitudinal portion and a circumferential portion, and wherein said radiopaque material coats both of said portions with substantially even thickness.

4. The stent according to claim 1, wherein said beta-emitting radioisotope emits substantially no alpha or gamma radiation.

5. The stent according to claim 1, wherein said radiopaque material comprises at least one material selected from the group consisting of platinum, iridium, and rhenium.

6. The stent according to claim 1, wherein said radiopaque material comprises at least one material selected from the group consisting of gold and tantalum.

7. The stent according to claim 1, wherein said beta-emitting radioisotope comprises sulfur-35.

8. The stent according to claim 1, wherein said beta-emitting radioisotope comprises phosphorous-32.

9. The stent according to claim 1, wherein said radiopaque material is between approximately 1 micron and approximately 5 microns thick.

10. The stent according to claim 1, wherein said radiopaque material is between approximately 1 micron and approximately 15 microns thick.

11. The stent according to claim 1, wherein said beta-emitting radioisotope is ion implanted to a depth of less than approximately 3000 angstroms into said radiopaque material.

12. The stent according to claim 1, wherein said beta-emitting radioisotope is ion implanted with a source strength of between approximately 0.1 microcuries and 10 microcuries.

13. The stent according to claim 1, wherein said beta-emitting radioisotope has a half life of less than approximately 100 days.

14. The stent according to claim 1, wherein said body has a tubular mesh shape.

15. The stent according to claim 1, wherein said body comprises a helical coil.

16. The stent according to claim 1, wherein said adhesion layer comprises a transition metal.

17. The stent according to claim 1, wherein said adhesion layer is between approximately 100 angstroms and approximately 3000 angstroms thick.

* * * * *